(12) United States Patent
Little

(10) Patent No.: US 9,084,678 B2
(45) Date of Patent: Jul. 21, 2015

(54) AUTOMATED IMPLANTABLE PENILE PROSTHESIS PUMP SYSTEM

(71) Applicant: AMS Research Corporation, Minnetonka, MN (US)

(72) Inventor: Eric F. Little, Shakopee, MN (US)

(73) Assignee: AMS Research Corporation, Minnetonka, MN (US)

( * ) Notice: Subject to any disclaimer, the term of this patent is extended or adjusted under 35 U.S.C. 154(b) by 261 days.

(21) Appl. No.: 13/745,063

(22) Filed: Jan. 18, 2013

(65) Prior Publication Data

US 2013/0190559 A1    Jul. 25, 2013

Related U.S. Application Data

(60) Provisional application No. 61/588,917, filed on Jan. 20, 2012.

(51) Int. Cl.
*A61F 5/00* (2006.01)
*A61F 2/26* (2006.01)

(52) U.S. Cl.
CPC ........................................ *A61F 2/26* (2013.01)

(58) Field of Classification Search
CPC ........................................................ A61F 2/26
USPC ..................................................... 600/38–41
See application file for complete search history.

(56) References Cited

U.S. PATENT DOCUMENTS

| | | | |
|---|---|---|---|
| 3,853,122 A | 12/1974 | Strauch et al. | |
| 3,954,102 A | 5/1976 | Buuck | |
| 4,009,711 A | 3/1977 | Uson | |
| 4,201,202 A | 5/1980 | Finney et al. | |
| 4,204,530 A | 5/1980 | Finney | |
| 4,222,377 A | 9/1980 | Burton | |
| 4,224,934 A | 9/1980 | Scott et al. | |
| 4,235,227 A | 11/1980 | Yamanaka | |
| 4,267,829 A | 5/1981 | Burton et al. | |
| 4,318,396 A | 3/1982 | Finney | |
| 4,342,308 A | 8/1982 | Trick | |
| 4,353,360 A | 10/1982 | Finney et al. | |
| 4,360,010 A | 11/1982 | Finney | |

(Continued)

FOREIGN PATENT DOCUMENTS

WO    WO02/38079    5/2002
WO    WO03/096929   11/2003

OTHER PUBLICATIONS

Gregory, John G. et al., The Inflatable Penile Prosthesis: Failure of the Rear Tip Extender in Reducing the Incidence of the Cylinder Leakage, The Journal of Urology, vol. 131, pp. 668-669 (Apr. 1984). cited by other.

(Continued)

*Primary Examiner* — John Lacyk
(74) *Attorney, Agent, or Firm* — Kagan Binder, PLLC

(57) ABSTRACT

An implantable penile prosthesis having an inflatable cylinder with at least one piezoelectric pump for transferring fluid between an integrated reservoir and pressure chamber within the inflatable cylinder. The piezoelectric pump includes an actuator powered by an inductor coil integrated into the inflatable cylinder allowing for wireless control of the inflation and deflation of the inflatable cylinder. An external control system having a corresponding inductive coil can be used to supply a magnetic field for creating a current in the inductor coil integrated into the inflatable cylinder.

17 Claims, 2 Drawing Sheets

(56) References Cited

U.S. PATENT DOCUMENTS

| | | |
|---|---|---|
| 4,364,379 A | 12/1982 | Finney |
| 4,369,771 A | 1/1983 | Trick |
| 4,378,792 A | 4/1983 | Finney |
| 4,383,525 A | 5/1983 | Scott et al. |
| 4,399,811 A | 8/1983 | Finney et al. |
| 4,399,812 A | 8/1983 | Whitehead |
| 4,404,968 A | 9/1983 | Evans, Sr. |
| 4,407,278 A | 10/1983 | Burton et al. |
| 4,412,530 A | 11/1983 | Burton |
| 4,424,807 A | 1/1984 | Evans, Sr. |
| 4,441,491 A | 4/1984 | Evans, Sr. |
| 4,449,520 A | 5/1984 | Palomar et al. |
| 4,457,335 A | 7/1984 | Trick |
| 4,523,584 A | 6/1985 | Yachia et al. |
| 4,532,920 A | 8/1985 | Finney |
| 4,550,719 A | 11/1985 | Finney et al. |
| 4,550,720 A | 11/1985 | Trick |
| 4,558,693 A | 12/1985 | Lash et al. |
| 4,559,931 A | 12/1985 | Fischell |
| 4,566,446 A | 1/1986 | Fogarty |
| 4,572,168 A | 2/1986 | Fischell |
| 4,574,792 A | 3/1986 | Trick |
| 4,590,927 A | 5/1986 | Porter et al. |
| 4,596,242 A | 6/1986 | Fischell |
| 4,602,625 A | 7/1986 | Yachia et al. |
| 4,604,994 A | 8/1986 | Sealfon |
| 4,611,584 A | 9/1986 | Finney |
| 4,622,958 A | 11/1986 | Finney |
| 4,651,721 A | 3/1987 | Mikulich et al. |
| 4,653,485 A | 3/1987 | Fishell |
| 4,664,100 A | 5/1987 | Rudloff |
| 4,665,903 A | 5/1987 | Whitehead |
| 4,671,261 A | 6/1987 | Fischell |
| 4,682,583 A | 7/1987 | Burton et al. |
| 4,682,589 A | 7/1987 | Finney |
| 4,718,410 A | 1/1988 | Hakky |
| 4,724,830 A | 2/1988 | Fischell |
| 4,726,360 A | 2/1988 | Trick et al. |
| 4,730,607 A | 3/1988 | Fischell |
| 4,766,889 A | 8/1988 | Trick et al. |
| 4,773,403 A | 9/1988 | Daly |
| 4,782,826 A | 11/1988 | Fogarty |
| 4,790,298 A | 12/1988 | Trick |
| 4,791,917 A | 12/1988 | Finney |
| 4,807,608 A | 2/1989 | Levius |
| 4,829,990 A | 5/1989 | Thuroff et al. |
| 4,881,530 A | 11/1989 | Trick |
| 4,895,139 A | 1/1990 | Hauschild et al. |
| 4,917,110 A | 4/1990 | Trick |
| 4,988,357 A | 1/1991 | Koss |
| 5,010,882 A | 4/1991 | Polyak et al. |
| 5,048,510 A | 9/1991 | Hauschild et al. |
| 5,062,416 A | 11/1991 | Stucks |
| 5,062,417 A | 11/1991 | Cowen |
| 5,063,914 A | 11/1991 | Cowen |
| 5,067,485 A | 11/1991 | Cowen |
| 5,101,813 A | 4/1992 | Trick |
| 5,112,295 A | 5/1992 | Zinner et al. |
| 5,114,398 A | 5/1992 | Trick et al. |
| 5,129,880 A | 7/1992 | Grundei |
| 5,141,509 A | 8/1992 | Burton et al. |
| 5,167,611 A | 12/1992 | Cowan |
| 5,171,272 A | 12/1992 | Levius |
| 5,250,020 A | 10/1993 | Bley |
| 5,263,981 A | 11/1993 | Polyak et al. |
| 5,344,388 A | 9/1994 | Maxwell et al. |
| 5,433,694 A | 7/1995 | Lim |
| 5,437,605 A * | 8/1995 | Helmy ............ 600/40 |
| 5,704,895 A | 1/1998 | Scott et al. |
| 5,851,176 A | 12/1998 | Willard |
| 5,895,424 A | 4/1999 | Steele, Sr. et al. |
| 6,387,071 B1 | 5/2002 | Constantz |
| 6,443,887 B1 | 9/2002 | Derus et al. |
| 6,533,719 B2 | 3/2003 | Kuyava et al. |
| 6,558,315 B1 | 5/2003 | Kuyava |
| 6,592,515 B2 | 7/2003 | Thierfelder et al. |
| 6,723,042 B2 | 4/2004 | Almli et al. |
| 6,730,017 B2 | 5/2004 | Henkel et al. |
| 6,733,527 B2 | 5/2004 | Koyfman |
| 6,911,003 B2 | 6/2005 | Anderson et al. |
| 6,929,599 B2 | 8/2005 | Westrum, Jr. |
| 6,935,847 B2 | 8/2005 | Kuyava et al. |
| 6,991,601 B2 | 1/2006 | Kuyava et al. |
| 7,066,877 B2 | 6/2006 | Kuyava |
| 7,066,878 B2 | 6/2006 | Francois |
| 7,131,944 B2 | 11/2006 | Jacquetin |
| 7,169,103 B2 | 1/2007 | Ling et al. |
| 7,244,227 B2 | 7/2007 | Morningstar |
| 7,250,026 B2 | 7/2007 | Kuyava |
| 7,350,538 B2 | 4/2008 | Kuyava et al. |
| 7,390,296 B2 | 6/2008 | Hans |
| 7,393,320 B2 | 7/2008 | Montpetit et al. |
| 7,407,480 B2 | 8/2008 | Staskin et al. |
| 7,438,682 B2 | 10/2008 | Henkel et al. |
| 7,491,164 B2 | 2/2009 | Choi et al. |
| 7,494,495 B2 | 2/2009 | Delorme et al. |
| 7,637,861 B2 | 12/2009 | Kuyava et al. |
| 7,901,346 B2 | 3/2011 | Kovac et al. |
| 8,585,580 B2 * | 11/2013 | Vaingast et al. ............ 600/37 |
| 2002/0033564 A1 | 3/2002 | Koyfman |
| 2002/0082473 A1 | 6/2002 | Henkel et al. |
| 2002/0082709 A1 | 6/2002 | Almli et al. |
| 2002/0091302 A1 | 7/2002 | Kuyava et al. |
| 2002/0103542 A1 | 8/2002 | Bilbo |
| 2003/0028076 A1 | 2/2003 | Kuyava et al. |
| 2003/0176762 A1 | 9/2003 | Kammerer |
| 2003/0220538 A1 | 11/2003 | Jacquetin |
| 2004/0039453 A1 | 2/2004 | Anderson et al. |
| 2004/0116774 A1 | 6/2004 | Migliari |
| 2004/0220447 A1 | 11/2004 | Morningstar |
| 2004/0249397 A1 | 12/2004 | Delorme et al. |
| 2004/0249473 A1 | 12/2004 | Delorme et al. |
| 2005/0080317 A1 | 4/2005 | Merade |
| 2005/0245787 A1 | 11/2005 | Cox et al. |
| 2005/0250977 A1 | 11/2005 | Montpetit et al. |
| 2005/0267325 A1 | 12/2005 | Bouchier et al. |
| 2006/0130848 A1 | 6/2006 | Carey |
| 2006/0235267 A1 | 10/2006 | George et al. |
| 2008/0114202 A1 | 5/2008 | Kuyava et al. |
| 2009/0012353 A1 | 1/2009 | Beyer |
| 2009/0105530 A1 | 4/2009 | Kuyava |
| 2009/0124851 A1 | 5/2009 | Kuyava et al. |
| 2009/0287042 A1 | 11/2009 | Almli et al. |

OTHER PUBLICATIONS

Hellstrom, WJG, Three-Piece INFLATABL4E Penile Prosthesis Components (Surgical Pearls on Reservoirs, Pumps, and Rear-Tip Extenders), Int'l J of Impotence Research, vol. 15, Suppl 5, pp. S136-138 (2003). cited by other.

Joseph, David et al., Bilateral Dislocation of Rear Tip Extenders From the Inflatable Penile Prosthesis, The Journal of Urology, vol. 1128, pp. 1317-1318 (Dec. 1982). cited by other.

Kim, Sae-Chul, M.D., Mechanical Reliability of AMS Hydraulic Penile Prostheses, Journal of Korean Medical Science, vol. 10, No. 6, pp. 422-425 (Dec. 1995). cited by other.

Levine, Laurence A. et al., Mechanical Reliability and Safety of, and Patient Satisfaction With the Ambicor Inflatable Penile Prosthesis: Results of a 2 Center Study, The Journal of Urology, vol. 166, pp. 932-937 (Sep. 2001). cited by other.

Malloy, Terrance R. et al., Improved Mechanical Survival With Revised Model Inflatable Penile Prosthesis Using Rear-Tip Extenders, The Journal of Urology, vol. 128, pp. 489-491 (Sep. 1982). cited by other.

Montague, Drogo K., Experience With Semirigid Rod and Inflatable Penile Prosthesis, The Journal of Urology, vol. 129, pp. 967-968 (May 1983). cited by other.

Mooreville, Michael et al., Implantation of Inflatable Penile Prosthesis in Patients With Severe Corporeal Fibrosis: Introdction of a New Penile Cavernotome, The Journal of Urology, vol. 162, pp. 2054-2054 (Dec. 1999). cited by other.

(56) References Cited

OTHER PUBLICATIONS

Mulcahy, John J., Distal Corporplasty for Lateral Extrusion of Penile Cylinders, The Journal of Urology, vol. 161, pp. 193-195 (Jan. 1999). cited by other.

Parulkar, B.G. et al., Revision Surgery for Penile Implants, Int. J. Impotence Res., vol. 6, pp. 17-23 (1994). cited by other.

Randrup, Eduardo R., M.D., Penile Implant Surgery: Rear Tip Extender That Stays BE3HIND, Urology, vol. XXXIX, No. 1, pp. 667-669 (Jan. 1992). cited by other.

Stein, Avi et al., Malleable Penile Prosthesis Removal Leaving Behind the Rear Tip Extenders: A Clinical Presentation, Urol. Intl, 50, pp. 119-120 (1993). cited by other.

AMS 700.TM. Inflatable Penile Prosthesis Product Line, Inservice Script brochure, American Medical Systems (1992). cited by other.

Ultrex/Ultrex Plus brochure, American Medical Systems, Inc. (1998). cited by other.

Description of Ultrex Fabric and Yarns (Mar. 30, 2001). cited by other.

Mentor Alpha.RTM. Inflatable Penile Prosthesis, Surgical Protocol, 15 pages (1998). cited by other.

Mentor Urology Products, 20 pages (May 1998). cited by other.

Mentor Alpha.RTM., The Results Are In, 14 pages (Apr. 1997). cited by other.

Mentor Alpha.RTM.Narrow Base, Simplifying Penile Implant Surgery by Making Difficult Cases More Manageable, 2 pages (Oct. 1996). cited by other.

Mentor.RTM. Acu-Form.RTM. Penile Prosthesis, 2 pages (Aug. 1997). cited by other.

Mentor.RTM. Acu-Form.RTM. Penile Prosthesis, Malleable Penile Prosthesis, Surgical Protocol, 8 pages (Sep. 1997). cited by other.

\* cited by examiner

AUTOMATED IMPLANTABLE PENILE PROSTHESIS PUMP SYSTEM

RELATED APPLICATION

The present application claims the benefit of U.S. Provisional Application No. 61/588,917 filed Jan. 20, 2012, which is incorporated herein in its entirety by reference.

FIELD OF THE INVENTION

The present invention is directed a system for inflating at least one inflatable cylinder of an implantable penile prosthesis. Specifically, the present invention is directed an automated pumping system for inflating the inflatable cylinder.

BACKGROUND OF THE INVENTION

Implantation of an implantable penile prosthesis (IPP) is a common surgical procedure for treating erectile dysfunction and other penile ailments. Typically, an IPP comprises at least one inflatable cylinder connected via kink resistant tubing to a pump with an integrated reservoir containing a quantity of fill liquid. In other versions, an IPP can alternatively comprise an inflatable cylinder connected by a pump to a separate reservoir for holding the quantity of fill liquid. Commercial IPP devices are available under the trade names AMBICOR and AMS 700 from American Medical Systems of Minnetonka, Minn. Typically, the entire IPP is implanted into the patient's body with the inflatable cylinder being placed in the corpus cavernosum and the pump being placed within the scrotum. The reservoir can also be placed within the scrotum or placed elsewhere within the pelvic region. To operate the IPP, the pump is manually actuated to transfer fill liquid from the integrated or implanted reservoir into the inflatable cylinder to fill and pressurize the inflatable cylinder.

While fully implanting the IPP within the body provides numerous advantages, operating the IPP is inherently more difficult due to the lack of direct access to the IPP. In particular, because the pump must be manually actuated through the scrotum, locating and operating the pump can be difficult. In addition, the position of the pump may cause the patient's to experience discomfort when operating the pump. An added drawback is that patients with comorbidities affecting their dexterity may be completely unable to operate the pump.

In addition to the practical difficulties of fully implanting the IPP, the implantation and positioning of the various components of the IPP itself can be a deterrent to those considering implanting an IPP. The implantation of an IPP requires an extensive surgical procedure involving not only the positioning of the inflatable cylinders, but also the implantation of the pump and the reservoir. The extensive surgical procedure for implanting an IPP can be a significant deterrent to those considering the implantation of the IPP.

SUMMARY OF THE INVENTION

The present invention is directed to an IPP having an inflatable cylinder comprising an integrated inflation system for inflating and pressurizing the inflatable cylinder. The inflation system comprises a piezoelectric pump for drawing fluid from a reservoir integrated into the inflatable cylinder and feeding the fluid into a pressure cylinder to expand and stiffen the inflatable cylinder. The piezoelectric pump and reservoir can be fully contained within the inflatable cylinder significantly reducing the extent and complexity of the surgery required for implanting the IPP. In addition, the automated piezoelectric pump replaces the manually operated mechanical pump used to inflate the inflatable cylinder in conventional IPP allowing for more precise inflation and pressurization of the pressure cylinder. The piezoelectric pump can be wirelessly controlled to control the inflation or deflation of the pressure cylinder.

An IPP, according to an embodiment of the present invention, comprises a pressure cylinder and an inflation system having a piezoelectric pump and an integrated reservoir. The piezoelectric pump comprises at least one piezoelectric actuator operably linked to a pump inductive coil. The pump inductive coil can be exposed to a magnetic field to create a current supplied to each piezoelectric actuator to cause the actuator to move fluid through the pump.

The piezoelectric pump can be operably linked to the pressure cylinder and can further comprise a first valve for controlling the direction of the fluid between the piezoelectric pump and pressure cylinder. The first valve can be actuated between an inflation position in which fluid can only enter the pressure cylinder for inflating the inflatable cylinder and a deflation position in which fluid can only exit the pressure cylinder for deflating the inflatable cylinder. Similarly, the pump can be operably linked to the integrated reservoir and further comprise a second valve controlling the direction of the fluid flow between the pump and the reservoir. The first and second valves can be operably linked such that fluid is transferred from the reservoir through the pump to the pressure cylinder and vice versa.

According to an embodiment, the IPP can be provided with an external control system having a control inductive coil and a power supply. The control inductive coil can be supplied with an electrical current from the power supply to generate a magnetic field for powering the pump when the control inductive coil is positioned proximate to the pump inductive coil. The control system can further comprise control circuitry for controlling the magnetic field generated to control the operation of the pump.

A method, according to an embodiment, comprises implanting an inflatable cylinder having an integrated pump powered by a pump inductive coil and adapted to transfer fluid between a pressure cylinder and an integrated reservoir. The method further comprises bringing a control inductive coil proximate to the pump inductive coil. The method also comprises supplying an electric current to the control inductive coil to generate a magnetic field for creating a corresponding electrical current in the pump inductive coil to actuate at least one piezoelectric actuator of the pump.

The above summary of the various representative embodiments of the invention is not intended to describe each illustrated embodiment or every implementation of the invention. Rather, the embodiments are chosen and described so that others skilled in the art can appreciate and understand the principles and practices of the invention. The figures in the detailed description that follow more particularly exemplify these embodiments.

BRIEF DESCRIPTION OF THE DRAWINGS

The invention can be completely understood in consideration of the following detailed description of various embodiments of the invention in connection with the accompanying drawings, in which.

Figure 1:
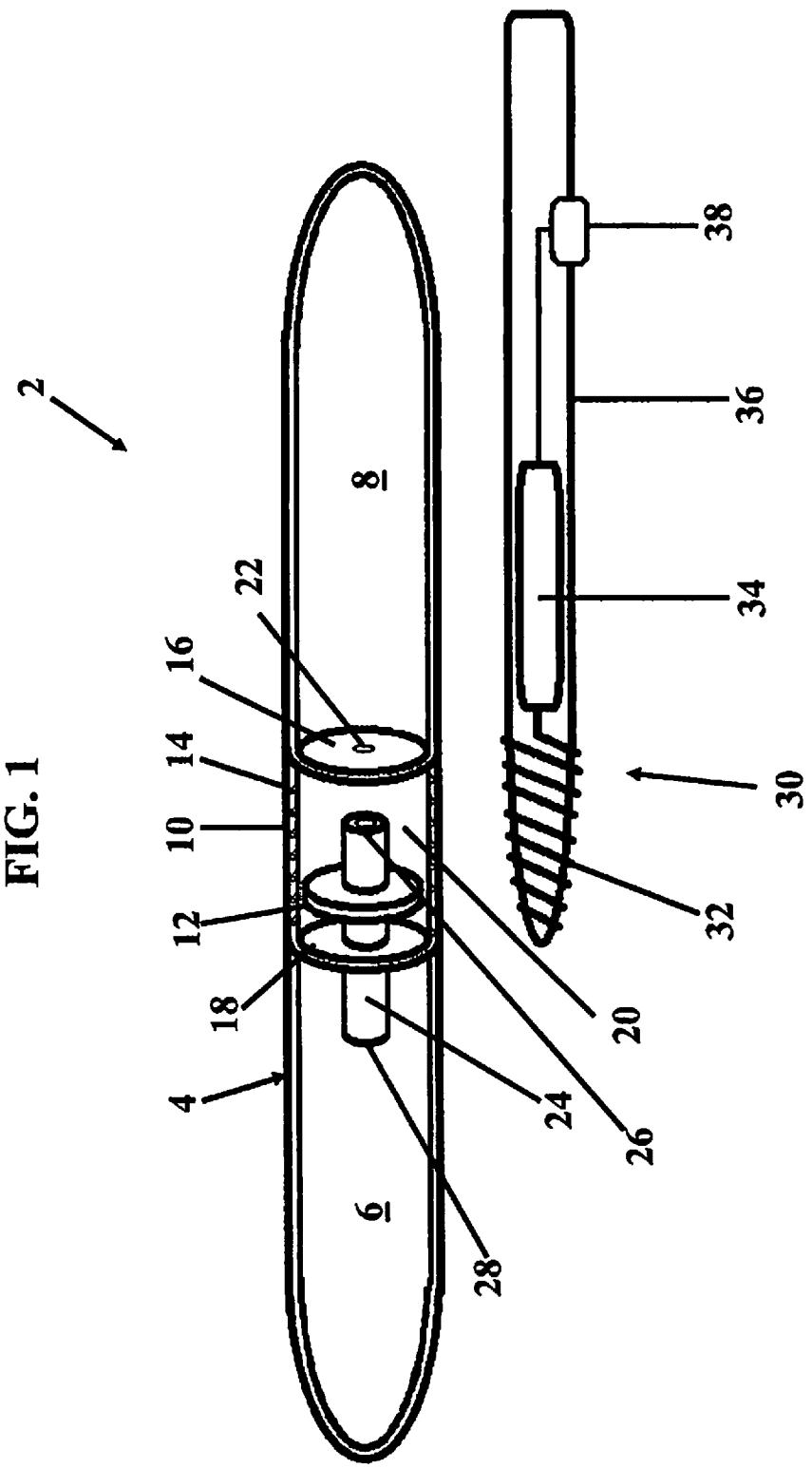
FIG. 1 is a partial cross-sectional side view of an implantable penile prosthesis and an external control device according to an embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

As shown in FIG. 1, an implantable penile prosthesis 2 ("IPP"), according to an embodiment of the present invention, comprises at least one inflatable cylinder 4 implantable within the corpus cavernosum. Each inflatable cylinder 4 comprises an elongated cylindrical body defining a fluid reservoir 6 at one end and an expandable pressure cylinder 8 positioned opposite the fluid reservoir 6. Each inflatable cylinder 4 further comprises an inflation system 10 operably linking the fluid reservoir 6 to the expandable pressure cylinder 8.

Figure 2:
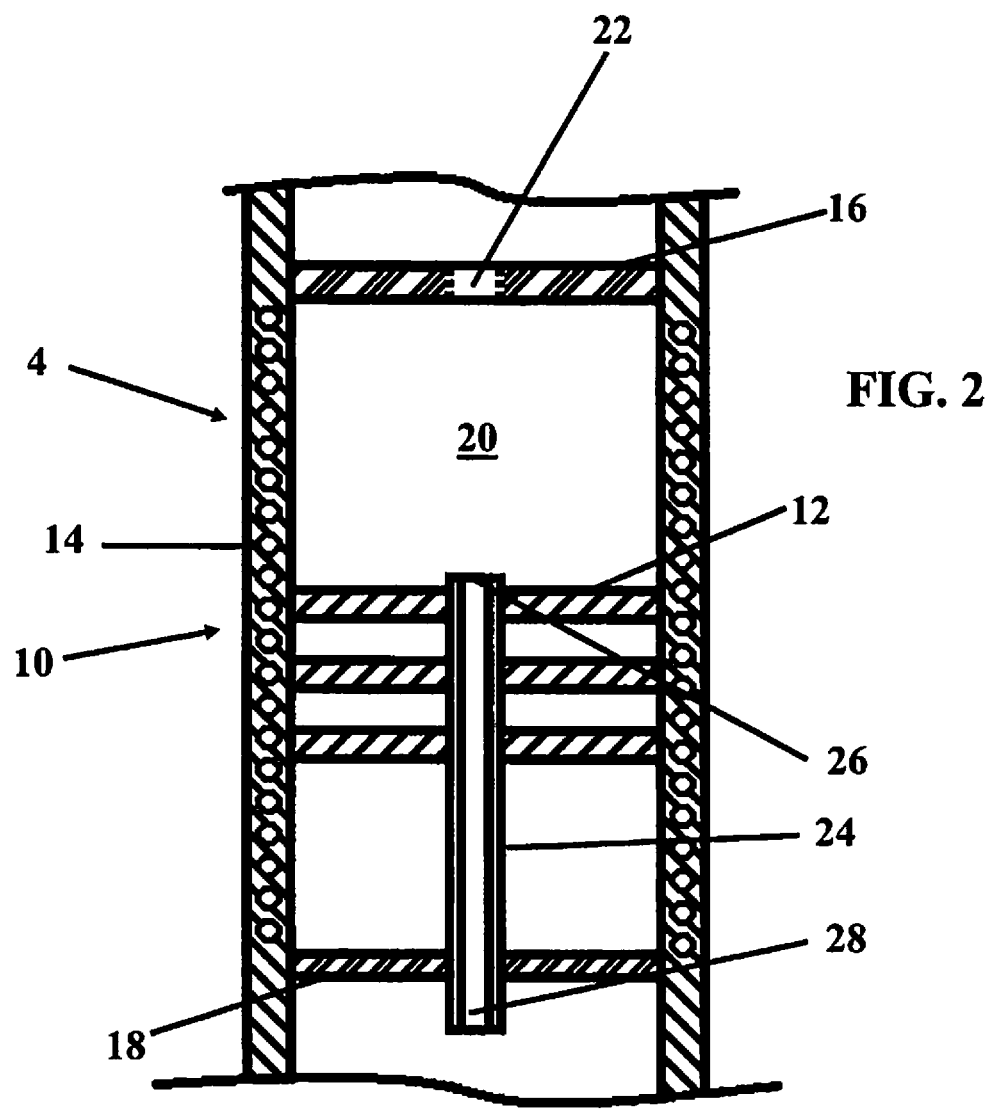
FIG. 2 is a cross-sectional side view of an inflation system for an implantable penile prosthesis according to an embodiment of the present invention.

As shown in FIG. 2, the inflation system 10 further comprises at least one piezoelectric actuator 12 and a pump inductive coil 14. The inflation system 10 further comprises a first septum 16 defining one wall of the pressure cylinder 8 and a second septum 18 defining one wall of the fluid reservoir 6. The first septum 16 and the second septum 18 cooperate to define a pump cavity 20 within the inflatable cylinder 4 between the fluid reservoir 6 and the pressure cylinder 8. The first septum 16 further comprises a first valve 22 switchable between an inflation position in which fluid can only flow into the pressure cylinder 8 and a deflation position in which fluid can only flow out of the pressure cylinder 8. The second septum 16 can further comprise a rod 24 extending through the second septum 16 and defining a channel 26 providing a fluid communication between the pump cavity 20 and the fluid reservoir 6. The rod 24 is positioned parallel to the longitudinal axis of the inflatable cylinder 4 to provide a guide for the piezoelectric actuators 12 during the movement of the actuators 12. The second septum 16 can further comprise a second valve 28 switchable between an inflation position in which fluid can only flow from the fluid reservoir 6 and a deflation position in which fluid can only flow into the fluid reservoir 6.

In operation, each of the actuators 12 is positioned on the rod 24 so as to move back and forth axially when supplied with an electrical current from the pump inductive coil 14. The back and forth motion of the actuators 12 draws fluid into the pump cavity 20 from either the reservoir 6 or the pressure cylinder 8 and expels fluid into the opposite chamber. The direction the first and second valves 22, 28 are oriented controls the direction of fluid through the inflation system 10. According to an embodiment, first and second valves 22, 28 can be positioned in a closed orientation to prevent any transfer of fluid between the pressure cylinder 8 and fluid reservoir 6.

As depicted in FIG. 1, according to an embodiment, the present invention can further comprise an external control system 30 for wireless controlling the operation of the IPP 2. The external control system 30 can further comprises a control inductive coil 32 and a power supply 34. The power supply 34 is adapted to supply current to the control inductive coil 32 to generate a magnetic field for generating a corresponding current in the pump inductive coil 14. According to an embodiment, the control system 30 can further comprise control circuitry for regulating the current supplied to the control inductive coil 32 to control the operation of the inflation system 10. The control circuitry can be adapted to pulse the current supplied to the control inductive coil 32 or automatically start or stop the current. As depicted in FIG. 1, the control system 30 can be mounted on a wand 36 allowing the user to position the control inductive coil 32 proximate to the pump inductive coil 14. According to an embodiment, the wand 36 can further comprise a switch 38 allowing a user to manually activate and deactivate the control inductive coil 32 to control the operation of IPP 2.

A method for inflating an IPP 2 can comprise providing at least one inflatable cylinder 4 having a fluid reservoir 6 and a pressure cylinder 8 with a pump cavity 20 defined there between. The method further comprising positioning at least one piezoelectric actuator 12 within the pump cavity 20, wherein each actuator 12 is operably linked to a pump inductive coil 14. Finally, the method further comprises directing a magnetic field toward the pump inductive coil 14 such that the coil 14 generates an electrical current that causes each actuator 12 to mechanically actuated, wherein the movement of the actuator 12 draws fluid from the fluid reservoir 6 and transfers the fluid to the pressure cylinder 8 to inflate and pressurize the pressure cylinder 8.

While the invention is amenable to various modifications and alternative forms, specifics thereof have been shown by way of example in the drawings and described in detail. It is understood, however, that the intention is not to limit the invention to the particular embodiments described. On the contrary, the intention is to cover all modifications, equivalents, and alternatives falling within the spirit and scope of the invention as defined by the appended claims.

The invention claimed is:

1. An implantable penile prosthesis, comprising:
   an inflatable cylinder enclosing a fluid reservoir,
   a piezoelectric pump,
   a pressure cylinder,
   a first septum comprising a first valve fluidly coupling the piezoelectric pump and the pressure cylinder for directing an inflation fluid into and out of the pressure cylinder,
   a second septum spaced from the first septum and defining a reservoir wall of the fluid reservoir, the second septum comprising a second valve fluidly coupling the piezoelectric pump and the pressure cylinder for directing the inflation fluid into and out of the fluid reservoir,
   a pump cavity positioned between the first septum and the second septum, and
   a rod extending through the second septum and defining a channel for fluid communication between the pump cavity and the fluid reservoir,
   wherein said piezoelectric pump selectively transfers fluid from the fluid reservoir to the pressure cylinder such that the inflatable cylinder selectively transitions between a flaccid disposition and an erect disposition.

2. The implantable penile prosthesis of claim 1, wherein the piezoelectric pump further comprises an actuator for selectively controlling the piezoelectric pump.

3. The implantable penile prosthesis of claim 2, wherein the actuator is operably coupled to a cylinder inductive coil, wherein the cylinder inductive coil interacts with a magnetic field to generate current for operation of the actuator.

4. The implantable penile prosthesis of claim 1,
   wherein the first valve and the second valve jointly direct flow of the inflation fluid between the fluid reservoir and the pressure cylinder.

5. The implantable penile prosthesis, of claim 1, wherein the first septum defines a pressure wall of the pressure cylinder; and
   wherein the piezoelectric pump is positioned within the pump cavity.

6. The implantable penile prosthesis of claim 1, wherein the first valve is mounted within the first septum and where the second valve is mounted within the second septum.

7. The implantable penile prosthesis of claim 1, in combination with
   an external control system for controlling operation of the piezoelectric pump.

8. The combination of claim 7, wherein the external control system comprises a control inductive coil and a power supply, wherein the power supply supplies control current to the control inductive coil to generates a control magnetic field.

9. The combination of claim 8, wherein the inflatable cylinder further comprise a cylinder inductive coil, wherein the cylinder inductive coil interacts with the control magnetic field to generate a cylinder current.

10. The combination of claim 9, wherein the piezoelectric pump further comprises a pump actuator and wherein the cylinder inductive coil is operably linked to the pump actuator, such that the cylinder current selectively controls operation of the piezoelectric pump.

11. The combination of claim 8, wherein the external control system further comprises a control circuit for selectively altering the control current.

12. The combination of claim 11, wherein the control circuit comprises a control switch for selectively activating and deactivating the generation of the control magnetic field.

13. The combination of claim 7, wherein the external control system comprises a hand held device such that the external control system can be positioned in proximity to the inflatable cylinder.

14. A method for treating erectile dysfunction, comprising:
   implanting a penile prosthesis within a corpus cavernosum, the penile prosthesis comprising:
   an inflatable cylinder enclosing a fluid reservoir,
   a piezoelectric pump,
   a pressure cylinder,
   a first septum comprising a first valve fluid coupling the piezoelectric pump and the pressure cylinder for directing an inflation fluid into and out of the pressure cylinder,
   a second septum spaced from the first septum and defining a reservoir wall of the fluid reservoir, the second septum comprising a second valve fluidly coupling the piezoelectric pump and the pressure cylinder for directing the inflation fluid into and out of the fluid reservoir,
   a pump cavity positioned between the first septum and the second septum, and
   a rod extending through the second septum and defining a channel for fluid communication between the pump cavity and the fluid reservoir,
   wherein said piezoelectric pump selectively transfers fluid from the fluid reservoir to the pressure cylinder such that the inflatable cylinder selectively transitions between a flaccid disposition and an erect disposition;
   generating a control magnetic field in proximity to the inflatable cylinder; and
   actuating the piezoelectric pump within the inflatable cylinder so as to selectively transfer an inflation fluid between the fluid reservoir and the pressure cylinder.

15. The method of claim 14, wherein the step of actuating the piezoelectric pump, further comprises:
   generating a pump current with a cylinder inductive coil within the inflatable cylinder, wherein the pump current operably controls a pump actuator linked to piezoelectric pump.

16. The method of claim 14, wherein the step of generating the control magnetic field in proximity to the inflatable cylinder, further comprises:
   positioning a handheld control system in proximity to the inflatable cylinder.

17. The method of claim 16, wherein the step of generating the control magnetic field in proximity to the inflatable cylinder, further comprises:
   directing a control circuit within the handheld control system to supply a control current from a power supply to a control inductive coil, said power supply and control inductive coil being internal to the handheld control system.

* * * * *

UNITED STATES PATENT AND TRADEMARK OFFICE
CERTIFICATE OF CORRECTION

PATENT NO. : 9,084,678 B2  
APPLICATION NO. : 13/745063  
DATED : July 21, 2015  
INVENTOR(S) : Little Page 1 of 1

It is certified that error appears in the above-identified patent and that said Letters Patent is hereby corrected as shown below:

IN THE CLAIMS:

Column 5, Line 1, Claim 5, delete "prosthesis," and insert -- prosthesis --, therefor.

Column 6, Line 1, Claim 14, delete "fluid coupling" and insert -- fluidly coupling --, therefor.

Signed and Sealed this  
Second Day of February, 2016

Michelle K. Lee  
*Director of the United States Patent and Trademark Office*